United States Patent [19]

Henry et al.

[11] 4,403,042

[45] Sep. 6, 1983

[54] DETECTION OF CELL MEMBRANE ANTIGENS AND CORRESPONDING ANTIBODIES

[75] Inventors: Wayne M. Henry, Elkhart, Ind.; Frank J. Mannuzza, Peotone; Makram M. Girgis, Bradley, both of Ill.

[73] Assignee: Miles Laboratories, Inc., Elkhart, Ind.

[21] Appl. No.: 409,456

[22] Filed: Aug. 19, 1982

[51] Int. Cl.³ .................... G01N 33/54; G01N 33/80
[52] U.S. Cl. .................... 436/519; 424/11; 436/520; 436/825
[58] Field of Search ............ 424/11; 436/520, 519, 436/825

[56] References Cited

U.S. PATENT DOCUMENTS

| | | |
|---|---|---|
| 3,955,925 | 5/1976 | Proksch et al. |
| 4,130,395 | 12/1978 | Choyssanthou ............... 424/11 X |
| 4,164,558 | 8/1979 | von Schulthess ............. 424/11 X |
| 4,259,207 | 3/1981 | Fruitstone ..................... 424/11 X |
| 4,290,774 | 9/1981 | Girgis et al. |
| 4,296,090 | 10/1981 | Graham, Jr. ................. 424/11 |
| 4,310,508 | 1/1982 | Siber ............................ 424/11 X |
| 4,319,882 | 3/1982 | Sharmd ........................ 424/11 X |
| 4,358,436 | 11/1982 | Graham, Jr. .................. 424/11 |

OTHER PUBLICATIONS

Transfusion, 12:353, (1972), "Scoring of Hemagglutination Reactions" by W. L. Marsch.
Proc. Natl. Acad. Sci., USA, 76(9):4438, (1979), "Passive Modulation of Blood-Group Antigens", Shinitzky & Souroujon.
Biochem. & Biophys. Res. Comm., 95(2):887, (1980), "Effects of Modulation . . . Expression" by M. K. Basu et al.
Nature, 224:510, (1969), "Influence of Polymers on the Efficacy of Serum . . . Agglutinins" by J. M. Jones et al.

*Primary Examiner*—Sidney Marantz
*Attorney, Agent, or Firm*—James D. McNeil

[57] ABSTRACT

A method for detecting weakly expressed cell membrane antigens or antibodies thereto which involves contacting cells to be tested with a lipoprotein substance substantially free of heteroagglutins and isoagglutins, containing cholesterol and phospholipid. The lipoprotein substance is obtained from animal plasma.

4 Claims, No Drawings

DETECTION OF CELL MEMBRANE ANTIGENS AND CORRESPONDING ANTIBODIES

BACKGROUND OF THE INVENTION

1. Field of the Invention

The body's immune system responds to a very large number of different foreign substances (antigens) either by producing antibodies directed against the antigen or cells that react specifically with the antigen.

The reaction between an antibody and its corresponding antigen, which can cause clumping or agglutination, forms the basis for numerous tests involving the detection of antigens or antibodies in fluid samples. Agglutination between an antibody and its corresponding antigen depends upon the formation of intercellular bridges which can sustain detectable agglutination.

Many cells have a small number of antibody combining sites on their surfaces, or the antibody combining sites have a low accessibility to antibodies, with the result that agglutination reactions between the antigens and antibodies do not readily occur. Such antigens are described as "weakly" expressed cell membrane antigens.

Examples of weakly expressed antigens include blood group antigens such as Rh ("D"), Lutheran (Lu), Kell (K), Duffy (Fy), Kidd (Jk), Diego (Di), Yt, Xg and Dombrock (Do). Most of these antigens were discovered by finding immume antibodies either in the mothers of infants with hemolytic disease or in patients who had received multiple transfusions.

Because of the deleterious effects of agglutination, it is desirable to detect weakly expressed antigens. Blood typing (grouping), cross-matching and antibody screening data are needed for safe transfusion and transplantation therapy, management of pregnancy, and evaluation of the newborn.

Other weakly expressed cell membrane antigens are present on other cells such as leucocytes and platelets. Leucocytes and platelets carry many antigens which usually cannot be demonstrated on red blood cells, but which are responsible for the rejection and elimination of foreign tissues. These antigens are collectively termed major histocompatibility complex, or human leucocyte antigens (HLA). The importance of HLA complex matching in renal and bone marrow transplantation is now well established, as is the need for HLA-compatible platelets or granulocytes (leucocytes) for transfusion into highly immunized patients.

Various media and techniques have been developed to promote agglutination for the purpose of detection of weakly expressed antigens. In the area of blood group antigens, one method involves postulated reduction of electrical conductance with high concentrations of hydrophilic colloid, e.g., bovine albumin. With enough antibodies, these tests are quite effective and can be used for Rh blood typing. However, such tests are not very sensitive and not of great value for detecting "weak" Rh and other alloantibodies or antigens. A second method involves breaking the disulfide bonds of the antibody and keeping the bonds from reforming by alkylating the disulfide bonds. Another method involves the use of a low ionic strength saline solution ("LISS"), e.g., glycine with a small amount of sodium chloride or other sodium salt, is added to human serum and cell mixture, and incubated at 37° C. for 15 minutes. Saline washing the addition of antihuman globulin reagent (AHG) or "Coombs" reagent is then carried out.

Several techniques have been developed to identify serum-defined HLA antigens. These tests include leucoagglutination, and microcytotoxicity.

The microcyctotoxicity test involves testing the permeability of cells after incubation with antibody and complement. If antibody is present, it combines with the target cells, as a consequence complement is fixed, and cell permeability increases, which kills the cell. The cell permeability is assessed by adding a solution of trypan blue or eosin which penetrates into dead cells, but leaves viable cells unstained.

Each of these methods involving detection of weakly expressed cell membrane antigens suffers the disadvantage of involving somewhat complicated test procedures. There is a need for a quick and simple method of increasing the sensitivity of detecting weakly expressed cell membrane antigens, including blood type leucocytes and platelets, and antibodies thereto.

2. Description of the Prior Art

Proc. Natl. Acad. Sci., USA, 76(9):4438 (1979) described the enrichment or depletion of membrane cholesterol by contacting the membrane with a media of lipid-modified serum. One composition used was finely dispersed synthetic cholesterol or egg lecithin in human serum medium mixtures; another mixture involved adding synthetic cholesterol or egg lecithin (in tetrahydrofuran or dimethylsulfoxide) to human serum. The authors found that as the cholesterol/phospholipid (C/P) ratio of the mixture was increased to greater than 1, the antigenic expression ("availability") of D antigens increased; conversely as the C/P ratio decreased to less than 1, the antigenic expression decreased. In order to achieve enrichment and subsequent enhancement of antigenic expression, contact of the media for a period of 10 hours at 37° C. was required.

Biochem. and Biophys. Res. Comm., 95(2):887 (1980) described the modification of the cholesterol content of Rh-positive and Rh-negative red cells and quantitated the D binding sites. The authors used the same synthetic cholesterol and egg lecithin dispersions described above and confirmed the above work, i.e., cholesterol enrichment (increase in C/P ratio) enhanced expression of D antigens.

Neither of these articles suggest or describe the detection of weakly expressed cell membrane antigens by use of a lipoprotein substance containing cholesterol and phospholipid, obtained from animal plasma. They also demonstrated a criticality of C/P ratio > 1.0 in order to enhance antigenic expression.

SUMMARY OF THE INVENTION

The present invention is directed to an improved method for detecting weakly expressed cell membrane antigens or antibodies thereto. The method includes the steps of adding suspended cells in a suitable medium to a body fluid which may or may not contain antibodies corresponding to said antigens and determining the presence or absence of antigens or antibodies thereto. The claimed improvement involves contacting the suspended cells with a lipoprotein substance substantially free of heteroagglutins and isoagglutins, containing cholesterol and phospholipid. The lipoprotein substance is obtained from animal plasma.

DETAILED DESCRIPTION OF THE INVENTION

The material used in the present invention is a medium composed primarily of lipoproteins of animal plasma origin. The lipoprotein substance contains cholesterol and phospholipid.

The lipoprotein substance used in the present invention can be easily prepared as taught in U.S. Pat. No. 4,290,774, which is incorporated herein by reference. It can also be prepared by alternative methods such as U.S. Pat. No. 3,955,925 as long as the hetero- and/or isoagglutinins are removed by commonly known methods in the art, e.g., heat, adsorption, etc.

Heteroagglutins are antibodies which will react with common antigens which occur on membranes of cells other than the species which produced the antibodies. For example, bovine plasma contains heteroagglutins which will agglutinate human red blood cells. Isoagglutins are antibodies which will react with common antigens which occur on membranes of cells of the same species which produced the antibodies. For example, type O human plasma which contains isoagglutins, i.e., anti-A, B, when mixed with type A, type B or type AB human red blood cells will agglutinate the red blood cells, even though the plasma and the cells are both of the same species. In order to avoid interfering agglutination in the detection of weakly expressed cell membrane antigens or antibodies thereto, it is necessary that the media in contact with the cells which are being tested be substantially free of heteroagglutins and isoagglutins.

The method disclosed in the '774 patent involves adsorbing the lipoprotein substance onto a silica adsorbant; separating the adsorbed lipoprotein from any excess solution; freezing and thawing the adsorbed lipoprotein; eluting the adsorbed lipoprotein at a pH of from 10 to 11.5; concentrating the lipoprotein to a desired concentration; optionally adjusting the pH from about 7.0 to 10.0; adjusting the salt concentration to about less than 0.05 M; heating to about 50° to 100° C. for a period of time from 5 minutes to 24 hours; adding an alkaline carbonate and alkaline earth salt to form a precipitate and removing the precipitate; adjusting the pH from about 6.5 to 9.0 and recovering purified lipoprotein substance.

The starting material can be any plasma or serum fraction that contains cholesterol. Suitable starting materials are obtained from mammalian sources and include bovine, horse, sheep, pig or human plasma, serum, or fraction thereof that contains cholesterol such as fibrinogen-poor plasma, i.e., a by-product of fibrinogen preparation such as Cohn Fraction I supernatant, an ammonium sulfate supernatant rich in lipoprotein, i.e., a 30 percent $(NH_4)_2SO_4$ supernatant, etc.

If the starting material is a lipoprotein-containing serum, the salt concentration is increased by the addition of a soluble salt, e.g., sodium citrate, to a final ionic strength of from about 0.25 to 1.0. Other suitable salts include sodium chloride, sodium phosphate, potassium phosphate, ammonium sulfate and sodium sulfate. Increase of the salt concentration of serum to the level referred to above has been found to increase the amount of lipoprotein adsorbed per unit of siliceous material added. Bovine or human plasma is normally collected by a method which includes addition of citrate as an anti-coagulant and it has been found that normally it is not necessary to increase the salt concentration.

The lipoprotein-containing starting material is maintained at a temperature of from 0° to 50° C., perferably from 15° to 25° C. The pH is adjusted to a range of from 5.5 to 9.0; preferably from 7.0 to 8.0.

Silica adsorbent in the form of microfine silica particles, commercially available under the trade designation Cabosil, from Cabot Corporation, 125 High Street, Boston, Mass. 02110, is added to the starting material in quantities from 1 to 50 gm per liter; preferably from 10 to 20 gm per liter.

The silica-lipoprotein-containing starting mixture is then mixed for a period of time of from 5 minutes to 6 hours; preferably from 3 to 4 hours. The silica particles preferentially absorb the lipoproteins present and form a silica/lipoprotein complex having a gel-like appearance. Excess solution is removed from the gel by conventional liquid/solid separation techniques, e.g., centrifugation or filtration.

The silica/lipoprotein gel is cooled at about −20° C. to 0° for a period of time sufficient to allow all of the gel to become frozen. Depending upon the container configuration and sample volume, from about 1 to 30 days is sufficient. The gel is allowed to thaw and the liquid that is expressed from the complex is discarded.

Optionally the gel is washed with distilled water or is suspended in dilute salt solution, e.g., 0.15 M sodium chloride, sodium acetate or sodium phosphate (approximately in a saline volume equal to twice the weight of the paste) at a pH of about neutral, e.g., pH 6.5 to 7.5, and allowed to settle. The supernatant is removed from the settled gel and the washing procedure is repeated two or three times with distilled water or dilute salt solution. The use of dilute salt solution ensures the solubility and removal of undesired proteins, e.g., euglobulins which are present in the interparticle space of the gel.

The washed gel is eluted by suspending it in 2 to 3 times its volume of distilled or deionized water at a pH adjusted to a range of from 10.0 to 11.5; preferably from 10.4 to 10.6. The mixture is stirred for about 3 to 4 hours and the pH maintained within the desired range. The mixture is then allowed to settle.

The supernatent is siphoned off and set aside. Elution of the gel, stirring and siphoning is repeated two more times and the supernatant portions combined.

The combined supernatant fractions are concentrated by conventional methods, e.g., precipitation by addition of salts and neutral polymers; adsorption/desorption methods, evaporation, or preferably by ultrafiltration. The supernatent is concentrated to any desired cholesterol concentration of from 50 to 3000 mg/dl preferably about 1000 to 2000 mg/dl.

Lipoprotein substance prepared as described above was determined to have the following characteristics:

Total protein less than 4.0 mg/dl
Inorganic phosphorus less than 1 mg/dl
Calcium less than 2 mg/dl
Glucose less than 20 mg/dl
Blood urea nitrogen less than 2 mg/dl
Total bilirubin less than 0.2 mg/dl
Sodium less than 25 mg/dl
Potassium less than 10 mg/l
Chloride less than 10 mg/l
Creatinine less than 0.2 mg/dl
Uric acid less than 0.2 mg/dl
Lactate dehydrogenase less than 10 M$\mu$/l
Creatinine phosphokinase less than 40 M$\mu$/l
α-glutamyltransferase less than 100 M$\mu$/l Serum glutamic oxalacetic transaminase less than 20 Mµ/l Glutamic pyruvate transaminase less than 30 Mµ/l The cholesterol/phospholipid ratio of the material was determined to be 0.65.

The tests described in Examples I-IV involve the use of saline-washed and saline-suspended red blood cells (RBC's) which contain weakly expressed antigens. Serial dilutions of known alloantibodies, for the corresponding weakly expressed RBC antigens, were dispensed into a titre series. Various concentrations of a lipoprotein substance substantially free of heteroagglutins and isoagglutins, containing cholesterol and phospholipid, obtained from animal plasma were added to each titre series. Detectable agglutination indicated the presence of the known antigen corresponding to the known alloantibody added.

A similar method can be used whereby known alloantibodies are used to detect unknown weakly expressed membrane antigens; this is designated as "typing". Conversely, the test can be used to detect low level alloantibodies by using known weakly expressed antigens; this is designated as "antibody screening" and "cross-matching."

In Examples I to III, agglutination was measured after incubation and centrifugation, but prior to the addition of any AHG reagent. In Example IV, agglutination was measured after incubation, centrifugation and addition of AHG reagent.

EXAMPLE I

Rh positive RCB's were obtained from human donors and centrifuged, decanted and exhaustively washed free of serum with phsiologic saline and reconstituted with saline to 2 to 5 percent. One part of the suspension was dispensed into five series of titre tubes. Subsequently 1 part of 5 percent saline suspended RBC's was added to each tube.

Five separate series of tubes were prepared by dispensing two parts of two-fold, saline, serial dilutions from 1:2 to 1:1024 of human D antibodies. These alloantibodies were obtained from human subjects who were immunized against D antigen, either by transfusion or previous pregnancy. To each series, 2 parts of varying amounts of lipoprotein substance prepared from bovine serum as described previously, containing cholesterol and phospholipid, dissolved to a final concentration of cholesterol as indicated in Table I, in 30 percent bovine albumin were also added. The bovine albumin-lipoprotein solutions were adjusted to a NaCl concentration of 0.15 M at a pH of 7.0. A titre series of samples containing 30 percent albumin with no lipoprotein substance was run as a control.

The tubes were mixed gently and incubated at 37° C. for about 15 minutes. The tubes were seriologically centrifuged at 1,000 rcf for 15 seconds, and the cell button gently dislodged from the tube and observed for degree of agglutination. The degree of agglutination was scored on a scale of from zero (O) (no reaction) to four (4) (strongest reaction). For scores lower than 1 yet clearly not truly negative, the terms "weak" (+) and "very weak" (±) were used. Test results obtained are summarized in Table I.

TABLE I

| 30% Albumin - Lipoprotein Substance RBC-Antibody Suspension Media | Anti-D Dilutions in Saline | | | | | | | | | |
|---|---|---|---|---|---|---|---|---|---|---|
| | 1:2 | 1:4 | 1:8 | 1:16 | 1:32 | 1:64 | 1:128 | 1:256 | 1:512 | 1:1024 |
| +0 | 3 | 3 | 3 | 1 | 1 | ± | ± | 0 | 0 | 0 |
| +15 mg/dl | 4 | 3 | 4 | 2 | 2 | 1 | 1 | ± | 0 | 0 |
| +44 g/dl | 3 | 4 | 4 | 4 | 3 | 2 | 1 | + | ± | 0 |
| +72 mg/dl | 4 | 4 | 4 | 4 | 2 | 2 | 2 | 1 | + | ± |
| +137 mg/dl | 4 | 4 | 4 | 4 | 3 | 3 | 2 | 2 | 2 | 0 |

C/P = 0.65
+ = slightly weaker than 1 yet not negative
± = trace, and barely detectable At a 1:2 dilution, the lipoprotein substance increased the sensitivity from 3 to 4 at each varying amount of lipoprotein substance. At a dilution of 1:64, the control sample reading was ± indicating the limits of detection of these systems under these conditions. In contrast, the presence of the lipoprotein substance increased the sensitivity of detection at 1:64 from 1 at the lowest concentration up to 3 at the highest concentration. Even at a serum dilution of 1:512, the presence of the lipoprotein substance allowed the detection of the D antigen at the highest concentration of cholesterol used.

EXAMPLE II

A procedure similar to that described in Example I was used, except that no albumin was added. The lipoprotein substance was tested against saline as a control and LISS as another alternative medium. The test results obtained are summarized in Table II.

TABLE II

| RBC-Antibody Suspension Media | Anti-D Dilutions in Saline | | | | | | | | | |
|---|---|---|---|---|---|---|---|---|---|---|
| | 1:2 | 1:4 | 1:8 | 1:16 | 1:32 | 1:64 | 1:128 | 1:256 | 1:512 | 1:1024 |
| Saline | 1 | 1 | 2 | + | 0 | 0 | 0 | 0 | 0 | 0 |
| LISS | 2 | 2 | 1 | + | 0 | 0 | 0 | 0 | 0 | 0 |
| Lipoprotein Substance (400 mg/dl expressed as cholesterol) | 3 | 4 | 4 | 3 | 1 | + | 0 | 0 | 0 | 0 |

C/P = 0.65

The above test results indicate the improved sensitivity obtained when the lipoprotein substance was added. At a dilution of 1:2, the lipoprotein substance increased the sensitivity over LISS of from 2 to 3. As the serum was diluted to 1:32, the saline and LISS both indicated negative for antigens, whereas the lipoprotein substance indicated a 1 value for hemagglutination, and at 1:64 a plus value, indicating increased sensitivity.

Nature, 224:510 (1969) indicated that polymerized albumin solutions enhanced agglutination more effectively than unmodified albumin. The following procedure was carried out to compare the sensitivity of modified albumin with lipoprotein substance.

EXAMPLE III

Polymerized bovine albumin was mixed with the lipoprotein substance to form a final concentration of 8 gm percent polymerized bovine albumin and 400 mg/dl (expressed as cholesterol) lipoprotein substance, and the salt concentration and pH adjusted as described in Example I. The albumin is commercially available from Miles Laboratories, Inc. The polymerized mixture described above was compared to a polymerized diluent mixture which did not contain the lipoprotein substance.

The human D antibodies used were reduced and alkylated antibodies, commercially available from Ortho Pharmaceuticals, Inc., Raritan, New Jersey, under the trade designation Nova Sera.

The test results obtained are summarized in Table III.

TABLE III

| Anti-D Diluent | Anti-D Dilutions in Saline | | | | | | | | |
|---|---|---|---|---|---|---|---|---|---|
| | 1:2 | 1:4 | 1:8 | 1:16 | 1:32 | 1:64 | 1:128 | 1:256 | 1:512 |
| 8 Percent Polymerized Albumin | 3 | 3 | 3 | 1 | 1 | + | ± | 0 | 0 |
| 8 Percent Polymerized Albumin + Lipoprotein Substance (400 mg/dl expressed as cholesterol) | 4 | 3 | 2 | 3 | 2 | 1 | + | ± | 0 |

At a dilution of 1:128, the control sample containing 8 percent polymerized albumin indicated a ± sensitivity; in contrast, the presence of the lipoprotein substance increased the sensitivity to +.

In order to determine the improvement in detecting blood type antigens in systems other than Rh ("D"), the following experiments on the Duffy (Fy) system, Kidd (Jk) system and Kell (K) system were carried out. Examples used as typical representatives of the systems are $Fy^a$, $Jk^a$ and $K+$ antigens.

EXAMPLE IV

Human serum samples were obtained from human donors known to have one of the above alloantibodies present.

The serum samples were diluted in saline and subjected to the procedure described in Examples I-III using lipoprotein substance except that after the serum/cell/media were incubated at +37° C. for 15 minutes, they were centrifuged and washed free of media with fresh saline 3 times and after the last decanting, AHG, commercially available from Ortho Diagnostics, under the trade designation Ortho Anti-Human Globulin Serum was added as per the manufacture's instructions, and the intensity of hemagglutination determined.

The agglutination reactions were scored as described in Transfusion, 12:353 (1972).

The test results obtained are summarized in Table IV.

TABLE IV

| RBC-Antibody Suspension Media | Titer Dilution in Saline | | | |
|---|---|---|---|---|
| | 1:2 | 1:4 | 1:8 | 1:16 |
| Anti-$Jk^a$ Dilution ($Jk^a+$, RBC's) | | | | |
| Saline (control) | 5 | 3 | 1 | 0 |
| Lipoprotein Substance (400 mg/dl expressed as cholesterol) | 9 | 9 | 4 | 2 |
| Anti-Kell Dilution (K+, RBC's) | | | | |
| Saline (control) | 9 | 7 | 3 | 0 |
| Lipoprotein Substance (400 mg/dl) | 9 | 8 | 6 | 2 |
| Anti-$Fy^a$ Dilution ($Fy^a+$, RBC's) | | | | |
| Saline (control) | 5 | 4 | 3 | 1 |
| Lipoprotein Substance (400 mg/dl) | 9 | 7 | 4 | 3 |

In the study involving the Jk and K system, at a dilution of 1:16, the saline control indicated a negative, i.e., no antibody detected. In contrast the addition of the lipoprotein substance gave a relatively strong reading, a value of 2.

In the study involving the $Fy^a$ system, at a dilution of 1:16, the sensitivity of the saline was 1, compared with a sensitivity of 3 in the presence of the lipoprotein substance.

These test results for the weakly expressed antigen listed in Table IV indicate that addition of the lipoprotein substance material increased the sensitivity of detecting the antibody.

Preliminary tests for detection of weakly expressed leucocyte antigens, i.e., serum-defined HLA antigens, were conducted, using a cytotoxicity test with the lipoprotein substance of Examples I-IV. The tests indicated that the lipoprotein substance greatly improved the detection of such antigens.

What is claimed is:

1. In a method for detecting weakly expressed cell membrane antigens or antibodies thereto which includes the steps of adding suspended cells in a suitable medium to a body fluid which may or may not contain antibodies corresponding to said antigens and determining the presence or absence of said antigens or antibodies thereto as a means for detecting the presence of said antigens or antibodies thereto, the improvement which comprises the step of contacting said suspended cells with a lipoprotein substance substantially free of heteroagglutins and isoagglutins, containing cholesterol and phospholipid, said lipoprotein substance being obtained from animal plasma.

2. A method as claimed in claim 1 wherein the cell membrane antigens are blood group antigens selected from the group consisting of Rhesus, Lutheran, Kell, Duffy, Kidd, Diego, Yt, Xg and Dombrock.

3. A method as claimed in claim 1 wherein the cell membrane antigens are human leucocyte antigens.

4. A method as claimed in claim 1 wherein the lipoprotein substance containing cholesterol and phospholipid is prepared by:
   (a) adsorbing a solution of a lipoprotein substance onto a silica adsorbant;
   (b) separating the adsorbed lipoprotein from any excess solution present;
   (c) freezing and thawing the adsorbed lipoprotein;
   (d) eluting the adsorbed lipoprotein at a pH of from about 10 to 11.5;
   (e) concentrating the lipoprotein obtained from step (d) to a desired concentration of cholesterol; adjusting the salt concentration to about less than 0.05 M;

(h) heating the cholesterol to a temperature of from about 50° to 100° C. for a period of about 5 minutes to 24 hours;

(i) adding an alkaline carbonate and an alkaline earth salt to form a precipitate and removing the precipitate;

(j) adjusting the pH of the cholesterol from about 6.5 to 9.0; and (k) recovering therefrom purified lipoprotein substance containing cholesterol and phospholipid.

* * * * *